US00PP16063P2

(12) United States Plant Patent
Danziger

(10) Patent No.: US PP16,063 P2
(45) Date of Patent: Oct. 25, 2005

(54) ***PETUNIA×CALIBRACHOA* PLANT NAMED 'DANCALIPET'**

(50) Latin Name: *Petunia sensu Wijsman×Calibrachoa La Llave*
Varietal Denomination: Dancalipet

(75) Inventor: Gabriel Danziger, Moshav Nir-Zvi (IL)

(73) Assignee: Danziger "Dan" Flower Farm (IL)

( * ) Notice: Subject to any disclaimer, the term of this patent is extended or adjusted under 35 U.S.C. 154(b) by 78 days.

(21) Appl. No.: 10/863,497

(22) Filed: Jun. 9, 2004

(51) Int. Cl.[7] ..... A01H 5/00
(52) U.S. Cl. ..... Plt./263
(58) Field of Search ..... Plt./263

(56) References Cited

PUBLICATIONS

Three groups of species in *Petunia sensu Jussieu* (Solanaceae) inferred from the intact seed morphology. Watanabe et al. American Journal of Botany.*

* cited by examiner

*Primary Examiner*—Anne Marie Grunberg
*Assistant Examiner*—Annette H Para
(74) *Attorney, Agent, or Firm*—Foley & Lardner, LLP

(57) ABSTRACT

A new and distinct *Petunia* plant named 'Dancalipet' particularly characterized by having red-purple flower color with a yellow veined tube, 35–40 mm across; small bush, cascading from hanging pots, compact growth, vigorous, well branched, slender foliage, good garden performance; lignified, persistent stems, woody at base; and displaying a profusion of flowers all summer long and well into autumn.

4 Drawing Sheets

Latin name of the genus and species of the plant claimed: *Petunia sensu Wijsman×Calibrachoa La Llave.*
Variety denomination: Dancalipet.

BACKGROUND OF THE INVENTION

The present invention relates to a new and distinct cultivar of *Petunia×Calibrachoa* plant, botanically known as *Petunia sensu Wijsman×Calibrachoa La Llave*, hereinafter referred to by the variety denomination 'Dancalipet'.

The new cultivar originated from a cross made in a controlled breeding program in Moshav Mishmar Hashiva, Israel. The female parent is *Petunia hybrida* designated '3082' (unpatented). The male parent is *Calibrachoa hybrida* designated '107' (unpatented). 'Dancalipet' was discovered and selected by the inventor, Gabriel Danziger, as a flowering plant within the progeny of the stated cross in a controlled environment in Moshav Mishmar Hashiva, Israel.

Asexual reproduction of the new cultivar by tip stem cuttings was first performed in June, 2003, in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Dancalipet' which in combination distinguish this *Petunia×Calibrachoa* as a new and distinct cultivar:

1. Red-Purple flower color with a yellow veined tube, 35–40 mm across;
2. Small bush, cascading from hanging pots, compact growth, vigorous, well branched, slender foliage, good garden performance;

3. Lignified, persistent stems, woody at base; and
4. Displaying a profusion of flowers all summer long and well into autumn.

Of the many commercial cultivars known to the present inventor, the most similar in comparison to 'Dancalipet' is the cultivar *Petunia* 'Danpetsweet' (U.S. Plant Pat. No. 10,822), commercially known as *Petitunia* 'Sweet Dream'. Table 1 shows a comparison between 'Dancalipet', *Petitunia* 'Sweet Dream', the female parent *Petunia hybrida* '3082' and the male parent *Calibrachoa hybrida* '107'.

TABLE 1

| Character | 'Dancalipet' | *Petitunia* 'Sweet Dream' | *Petunia hybrida* '3082' | *Calibrachoa hybrida* '107' |
|---|---|---|---|---|
| Flower color | Red-Purple | Red-Purple | Red-Purple | Red-Purple |
| Flower size (cm) | 3.5–4.0 | 4.0 | 3.5 | 3.0 |
| Growth vigor | High | High | High | Medium |
| Growth habit | Bush cascading | Bush cascading | Cascading | Bush cascading |
| Leaf size (cm) | 5.0–5.5 | 8.0 | 9.0 | 3.0 |
| Lignified stem | Yes | No | No | Yes |

'Dancalipet' has not been observed under all possible environmental conditions. The phenotype of the new cultivar may vary significantly with variations in environment such as temperature, light intensity, and day length without any change in the genotype of the plant.

BRIEF DESCRIPTION OF THE DRAWING

The accompanying photographic drawings illustrate the overall appearance of the new variety showing the colors as true as is reasonably possible with color reproductions of this type.

The first photograph shows a 'Dancalipet' plant in its entirety in a hanging pot.

The second photograph is a close up of a single 'Dancalipet' flower.

The third photograph is a close-up of a 'Dancalipet' bud.

The fourth photograph depicts a comparison of a 'Dancalipet' flower on the upper left hand side, a flower of the female *Petunia hybrida* '3082' on the upper right hand side; a flower of the male *Calibrachoa hybrida* '107' on the lower left hand side; and a flower of the comparison cultivar 'Sweet Dream' on the lower right hand side.

DETAILED BOTANICAL DESCRIPTION

The following observations, measurements and values describe the new cultivar as grown in Moshav Mishmar Hashiva, Israel under conditions which closely approximate those generally used in commercial practice. 'Dancalipet' can be used as a pot plant and a bedding plant. For optimal growth conditions, 'Dancalipet' should be grown outdoors in moderate climate, exposed to full sunlight, with regular irrigation and fertilization; and grown indoors in the winter. A fully grown plant takes 3 months. 'Dancalipet' blooms year-round in moderate climate.

Color references are made to The Royal Horticultural Society Colour Chart (R.H.S.) 2001, except where general colors of ordinary significance are used. Color values were taken under daylight conditions at approximately noon in Moshav Mishmar Hashiva, Israel. The age of the plant described is 6 weeks.

Parentage:
- *Male parent.*—*Calibrachoa hybrida* '107'.
- *Female parent.*—*Petunia hybrida* '3082'.

Classification:
Botanical: *Petunia sensu Wijsman*×*Calibrachoa La Llave.*
Commercial: *Petunia*×*Calibrachoa* cv. Dancalipet.
Propagation: Stem cuttings.
Plant:
General appearance and form:
- *Height.*—20–25 cm.
- *Spread.*—60–80 across.
- *Growth habit.*—Bush cascading.
- *Growth rate.*—Fully grown plant in 3 month during summer.
- *Branching habit and description.*—Freely, well branched.
- *Flowering response.*—Long day facultative.
- *Flowering season.*—Year round in moderate climate.
- *Winter hardiness/weather tolerance.*—Frost tender.
- *Lastingness of the individual bloom.*—5–7 days.
- *Rooting habit.*—Freely.
- *Time to initiate roots.*—7–10 days.
- *Time to produce a rooted cutting.*—3 weeks.
- *Fragrance.*—None.

Stem description:
- *Length.*—50–60 cm.
- *Diameter.*—4 mm.
- *Internode length and color.*—1.5–3.5 cm, Yellow-green 144-B.
- *Strength.*—Lignified, persistent at stem base.
- *Branching.*—Well branched.
- *Pubescence.*—Yes.

Foliage:
- *Overall shape of leaf.*—Lanceolate.
- *Arrangement.*—Alternate.
- *Apex.*—Acuminate.
- *Base.*—Obtuse.
- *Length.*—50–55 mm.
- *Width.*—20–25 mm.
- *Margin.*—Entire.
- *Texture.*—Lustrous.
- *Color of upper surface.*—Green 137-B (both mature and immature).
- *Color of lower surface.*—Green 137-C (both mature and immature).
- *Venation color.*—None.
- *Petiole.*—Length: 5 mm. Diameter: 2 mm. Color: Yellow-Green 144-A.

Inflorescence:
- *Flower longevity.*—5–7 days.
- *Flower size.*—35–40 mm across.
- *Flower shape.*—Rounded, corolla united with 5 lobes and a long straight tube.
- *Average number of flowers per lateral branch.*—40–50 in varying developing stages.
- *Petals.*—Number: 5, fused at the base. Shape: Salver form. Size: 35 mm long; 20 mm wide. Apex: Blunt. Margin: Wave. Color: Upper surface: Red-Purple 74-A. Lower surface: Purple 75-A.
- *Sepals.*—Number: 5. Shape: Deeply incised, 5 lobes, cup shaped. Size: Of a single sepal: 12/1.5 mm. Apex: Truncate. Margin: Entire. Texture: Lustrous. Color: Upper surface: Green 141-A. Lower surface: Green 143-B.
- *Bud.*—Rate of opening: 7–10 days, depending on weather conditions. Color: Top ⅓ closest to greyed purple RHS 187A; bottom ⅔ green RHS 137 B, 138 B and 138 C. Shape: Oblong. Length: 25 mm. Diameter: 6–8 mm.
- *Peduncle color and length.*—2–3 cm, Yellow-Green 144-A.

Reproductive organs:
- *Stamen.*—5 in number; Yellow-Green 145-A.
- *Anthers.*—Yellow-Green 145-C.
- *Stigma.*—Yellow-Green 144-A.
- *Ovary.*—Yellow-Green 144-B.
- *Pollen.*—Yellow-Green 145-C.
- *Seed.*—None observed.
- *Fruit.*—None observed.

Disease/pest resistance/susceptibility: No observations made to date.

I claim:

1. A new and distinct *Petunia*×*Calibrachoa* plant named 'Dancalipet' as illustrated and described herein.

* * * * *

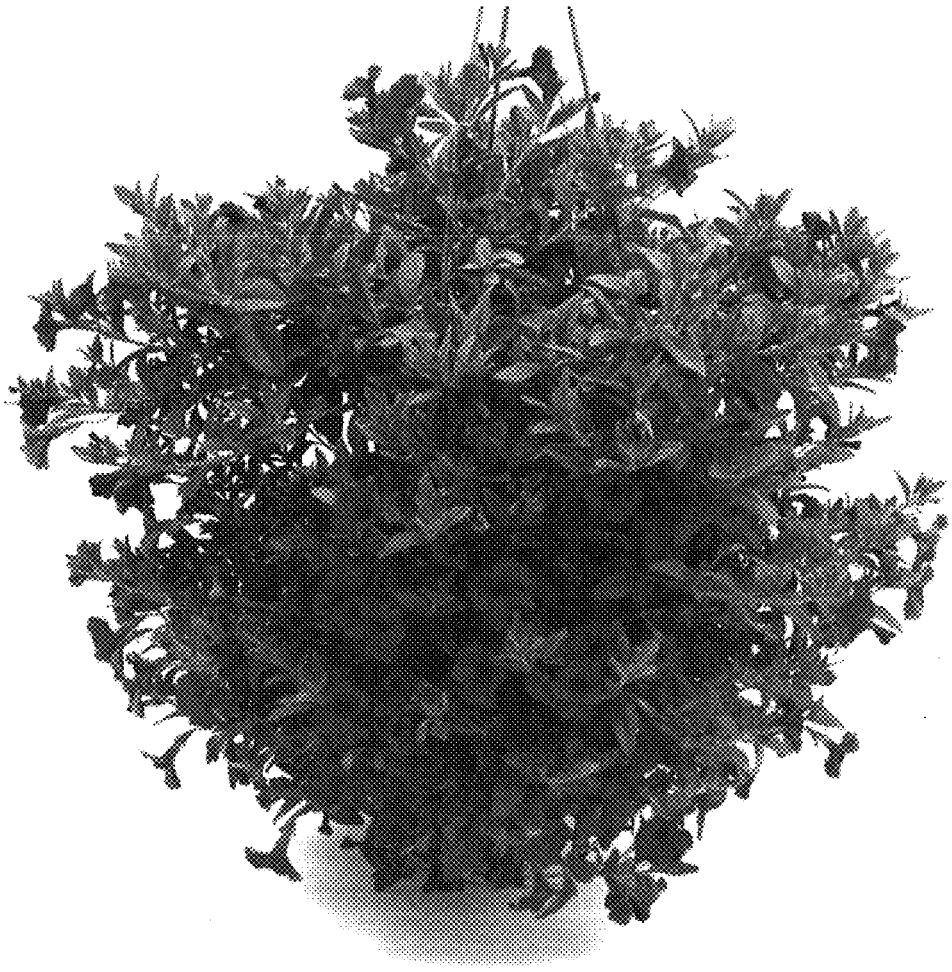

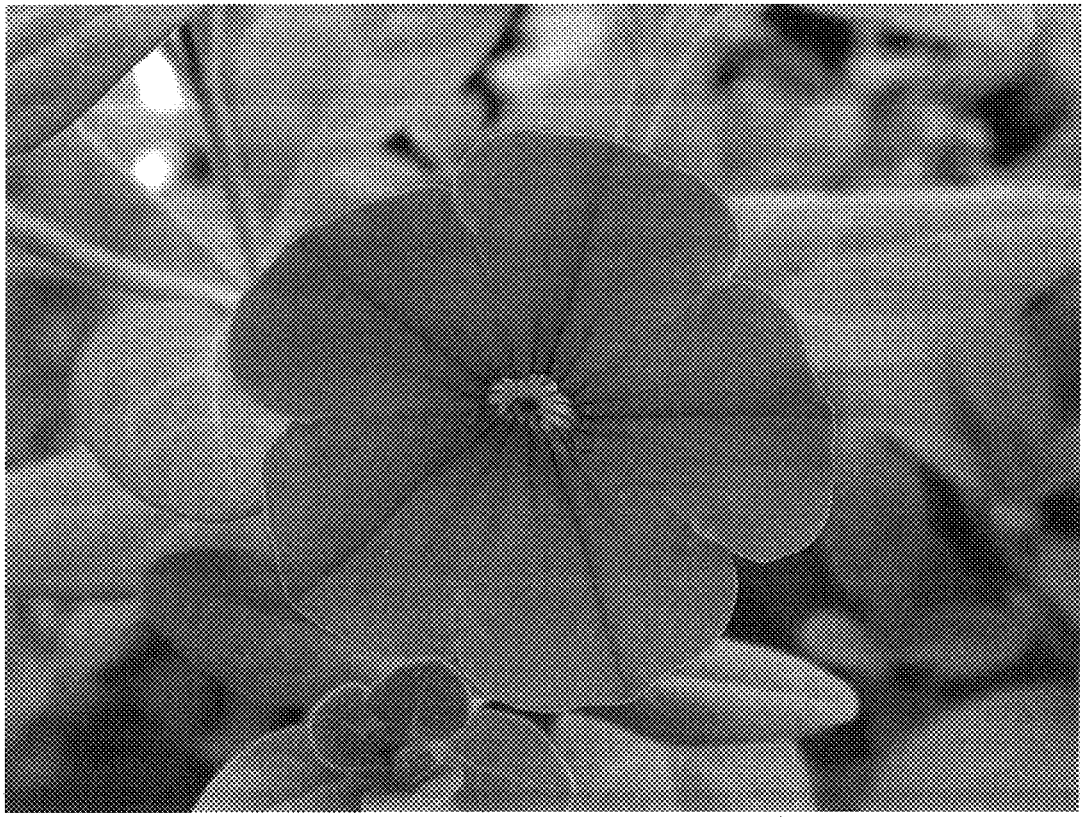

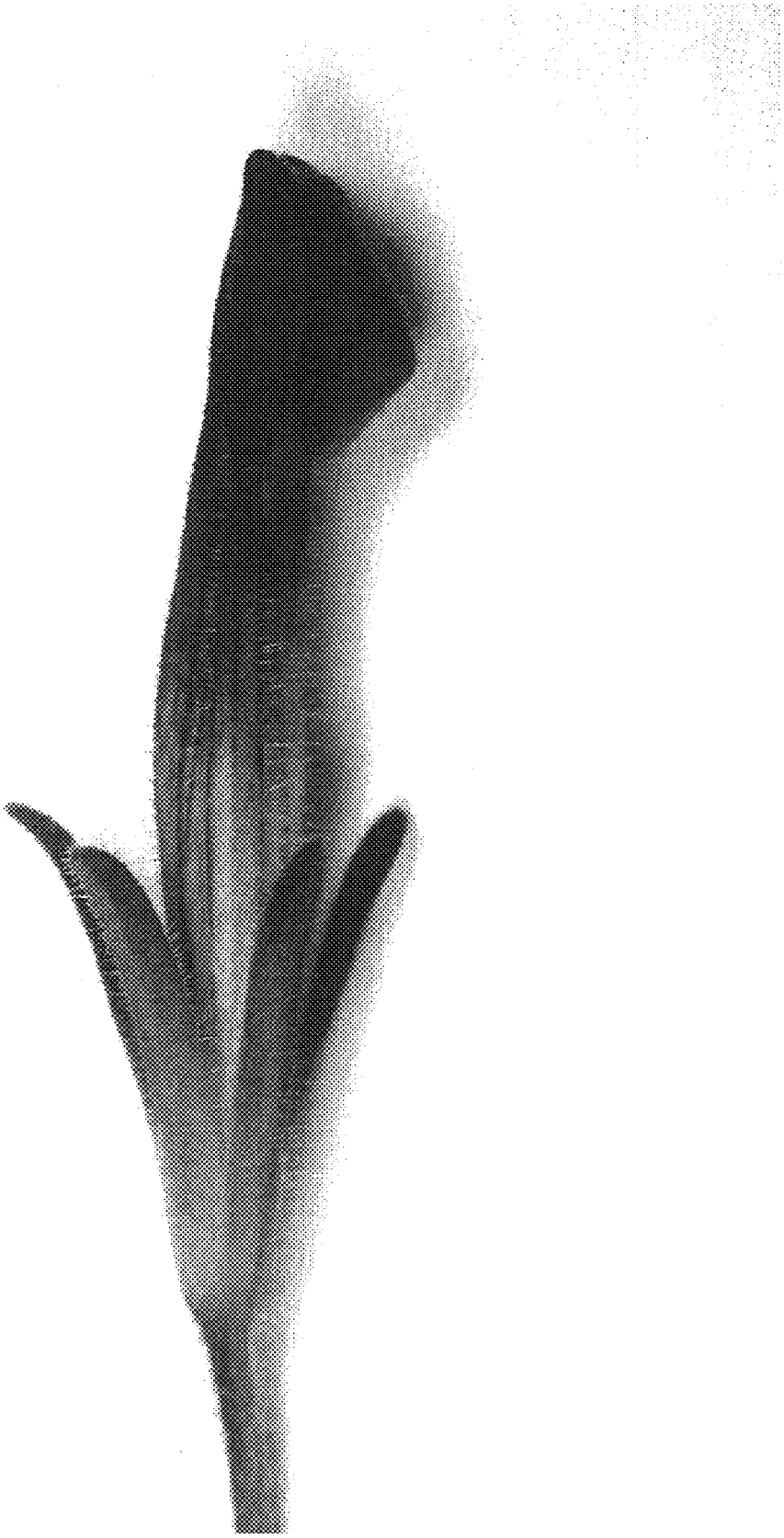

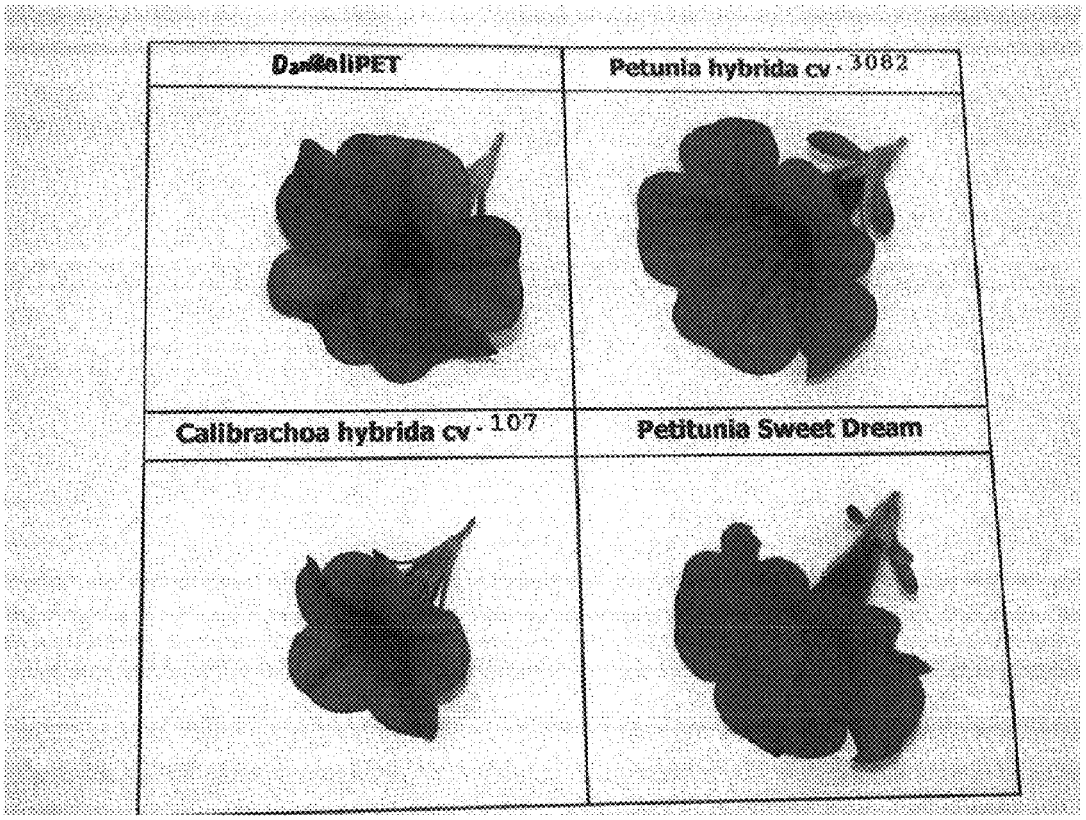
DanielliPET
Petunia hybrida cv - 3082
Calibrachoa hybrida cv - 107
Petitunia Sweet Dream